United States Patent
White et al.

(10) Patent No.: US 9,147,398 B2
(45) Date of Patent: Sep. 29, 2015

(54) HYBRID INPUT DEVICE FOR TOUCHLESS USER INTERFACE

(71) Applicant: Nokia Corporation, Espoo (FI)

(72) Inventors: Richard White, Huntingdon (GB); Jani Kivioja, Cambridge (GB); Andrew Peter Matthews, Cambridge (GB); Michael Astley, Cambs (GB); Stefano Marco Borini, Cambridgeshire (GB)

(73) Assignee: Nokia Technologies Oy, Espoo (FI)

( * ) Notice: Subject to any disclaimer, the term of this patent is extended or adjusted under 35 U.S.C. 154(b) by 341 days.

(21) Appl. No.: 13/747,729

(22) Filed: Jan. 23, 2013

(65) Prior Publication Data

US 2014/0207467 A1      Jul. 24, 2014

(51) Int. Cl.
| | |
|---|---|
| *G10L 15/00* | (2013.01) |
| *G10L 17/00* | (2013.01) |
| *G10L 15/24* | (2013.01) |
| *G06F 3/01* | (2006.01) |
| *G01N 33/497* | (2006.01) |
| *G06K 9/00* | (2006.01) |

(52) U.S. Cl.
CPC . *G10L 15/24* (2013.01); *G06F 3/01* (2013.01); *G01N 33/497* (2013.01); *G06K 9/00496* (2013.01)

(58) Field of Classification Search
CPC ......... G10L 15/24; G10L 15/25; G10L 17/22; G10L 17/26; G01N 33/497; G06F 1/32; G06F 3/16; G06F 21/32; H04W 52/02
USPC .................................. 704/231–257, 270–275
See application file for complete search history.

(56) References Cited

U.S. PATENT DOCUMENTS

| | | | |
|---|---|---|---|
| 6,130,663 A | 10/2000 | Null | 345/158 |
| 7,620,316 B2 | 11/2009 | Boillot | 396/429 |
| 7,774,204 B2 | 8/2010 | Mozer et al. | 704/275 |
| 7,978,091 B2 | 7/2011 | Boillot | 340/686.1 |
| 8,160,311 B1 * | 4/2012 | Schaefer | 382/118 |
| 2002/0080132 A1 | 6/2002 | Dai et al. | 345/212 |
| 2004/0092297 A1 | 5/2004 | Huang | 455/575.7 |
| 2009/0060287 A1 | 3/2009 | Hyde et al. | 382/118 |

(Continued)

FOREIGN PATENT DOCUMENTS

| | | |
|---|---|---|
| EP | 2479963 A1 | 7/2012 |
| EP | 2485128 A2 | 8/2012 |

(Continued)

OTHER PUBLICATIONS

Sensirion; "Datasheet SHT21S, Humidity and Temperature Sensor IC"; Jan. 10, 2013; pp. 1-10, particularly Product Summary & Sections 5.2-5.3; Retrieved from the Internet: <URL: http://web.archive.org/web/20130110082155/http://www.sensirion.com/fileadmin/user_upload/customers/sensirion/Dokumente/Humidity/Sensirion_Humidity_SHT21S_SDM_Datasheet_V3.pdf [Retrieved on May 19, 2014].
Cote, et al., "Langmuir-Blodgett Assembly of Graphite Oxide Single Layers", 131 (2009), (pp. 1043-1049).

*Primary Examiner* — Jesse Pullias
(74) *Attorney, Agent, or Firm* — Harrington & Smith (57) ABSTRACT

An apparatus includes a breath sensor including a film configured to sense a variation in electrical impedance based on a moisture gradient and output the sensed variation as an output signal; and a controller configured to process the output signal from the breath sensor. The apparatus is configured to receive the output signal from the breath sensor and provide a signal in response thereto.

20 Claims, 6 Drawing Sheets

(56) References Cited

U.S. PATENT DOCUMENTS

| | | | |
|---|---|---|---|
| 2009/0082884 A1 | 3/2009 | Bonnat | 700/83 |
| 2010/0280983 A1 | 11/2010 | Cho et al. | 706/46 |
| 2012/0331566 A1 | 12/2012 | Lection et al. | 726/28 |
| 2013/0006068 A1 | 1/2013 | Gemer et al. | 600/314 |
| 2014/0004908 A1 | 1/2014 | Park et al. | 455/566 |

FOREIGN PATENT DOCUMENTS

| | | |
|---|---|---|
| JP | 2001-309430 A | 11/2001 |
| JP | 2005-214713 A | 8/2005 |
| WO | WO 03/043684 A1 | 5/2003 |
| WO | WO-2012/178071 A2 | 12/2012 |

\* cited by examiner

HYBRID INPUT DEVICE FOR TOUCHLESS USER INTERFACE

BACKGROUND

1. Technical Field

The exemplary and non-limiting embodiments disclosed herein relate generally to touchless user interfaces and, more particularly, to a breath-controlled wake up of a data input system.

2. Brief Description of Prior Developments

Various types of touchless user interface devices are known. Touchless systems for the activation of a controlled element based on optical sensing and triangulation are known, as are systems for controlling the operation of a device by voice. One type of system for controlling the operation of a device by voice is a speech recognition system having a low power wake up circuit (a low power audio channel coupled to both a microphone and a second standard audio channel, with a processor to switch between the two audio channels).

SUMMARY

The following summary is merely intended to be exemplary and is not intended to limit the scope of the claims.

In accordance with one aspect, an apparatus comprises a sensor comprising a sensing film configured to provide a signal based upon a user's breath and a controller operably associated with the sensor. The controller is configured to receive the signal based upon the user's breath.

In accordance with another aspect, another apparatus comprises a breath sensor comprising a graphene oxide film configured to sense a variation in electrical impedance based upon a moisture gradient and output the sensed variation as an output signal, and a controller configured to process the output signal from the breath sensor. The apparatus is configured to receive the output signal from the breath sensor and provide a signal in response thereto.

In accordance with another aspect, a method comprises providing a user interface comprising a sensor that includes a film configured to provide a signal as a result of moisture, and a controller operably associated with the sensor, the controller comprising a processor; receiving an input from a user at the user interface, the input comprising moisture in the form of humidity from a breath from the user; producing the signal from the input based upon the breath of the user; and receiving the signal produced from the input from the breath of the user at the processor and processing the signal.

BRIEF DESCRIPTION OF THE DRAWINGS

The foregoing aspects and other features are explained in the following description, taken in connection with the accompanying drawings, wherein.

DETAILED DESCRIPTION OF THE EMBODIMENTS

Touchless user interfaces (UIs) such as gesture swipe, proximity, and speech recognition are some of the considered technologies for the development of future electronic devices. Other considered technologies are those utilizing breath sensing mechanisms that activate devices from power managed modes.

One of the most natural implementations of a touchless UI is the use of speech recognition. Exemplary speech recognition systems use a microphone to convert sound waves into electrical signals, which are then interpreted by a processor using speech recognition algorithms. In such systems, however, the microphone and processor setup is often excessively power hungry and not suitable for use in an "always on" mode in a portable consumer electronics device such as a mobile phone. To combat this, existing microphone/processor setups are generally awakened by a secondary user input, typically by the user pressing a button before speaking. When a button is pressed, the UI is no longer truly touchless and is therefore less natural and less intuitive to use. When the secondary user input is, on the other hand, a voice input, the microphone may struggle to differentiate between the user's voice and background noises and be unable to discriminate when the device is being spoken into, which limits use of the UI in noisy environments. Furthermore, a microphone typically has limited sensitivity for the detection of subtle variations in air velocity and humidity emitted by a user when the user speaks, such air velocity and humidity being dependent upon the state of emotion of the user, physical condition, and identity. Detection and differentiation of these additional components can enable a much richer analysis of words spoken by the user.

Exemplary embodiments of a touchless UI in the form of a speech recognition system defined by a hybrid user input device are disclosed herein. The hybrid user input device includes a sensor incorporating a thin film defined by layers of graphene oxide (hereinafter "GO") and an associated controller. The controller includes a processor that can be activated via a moisture gradient on the GO film. Some exemplary embodiments of the hybrid user input device may also include a microphone. Software code associated with the processor is configured to interpret the responses of the sensor and possibly combine such responses with responses from the microphone, if present. In alternate exemplary embodiments, the sensor may comprise materials other than GO, such as graphene, functionalized graphene, fluorographene, molybdenite, boron nitride, combinations of the foregoing materials, and the like.

The sensor incorporating the thin film of GO may be used to wake the hybrid user input device from a low-power operation (or "sleep" mode in which the hybrid user input device is powered down to conserve energy) and may operate on lowlatency humidity. Additionally, or in the alternative, the sensor may provide for background noise reduction, emotional state recognition, and/or user identification.

In one embodiment, when a user begins speaking to the hybrid user input device, the GO film-based sensor provides a response based on moisture released into the environment by the user. The response provided by the sensor is generally a variation of electrical impedance that is detected within a relatively short period of time. For example, such a detection of response is generally considered "ultrafast" and is on the order of about 10-12 milliseconds (ms), as described herein. The response activates the controller and initiates the touchless interaction of the system. A speech recognition function associated with the processor can be substantially instantaneously activated via the response of the sensor as the user begins speaking even if the device is in a sleep mode.

In some embodiments, the response time of the sensor may allow for an analysis (e.g., by the processor) of air directed into the GO film by the user while the user speaks. During such an analysis, changes in profiles of selected words are noted with regard to changes in the emotional state of the user. In particular, similar words, when spoken with different intonations, have different frequencies and amplitudes that provide different velocity signatures as well as different thermal and moisture signatures. The sensor may be configured to accordingly "learn" words based on velocity, thermal, and moisture signatures to distinguish different emotions (mood recognition) of the user. The system employing the sensor may also continually improve the learned words by continual analysis of frequency and amplitude of sounds emitted by the user as well as analysis of gradients in temperature and moisture content. The system and sensor may also be configured to compensate for temperature and moisture gradients with respect to background moisture levels (e.g., ambient humidity).

In some embodiments, moisture analysis of learned spoken words can be used for user identification. This aspect allows the sensor (either alone or in combination with a microphone) to be used as a security measure to lock or unlock a device such as a phone. When moisture analysis is used as a security measure to lock or unlock a phone, manual input of a security measure such as a password or code is obviated, and a user's breath may be sufficient to unlock the phone to accept a call. If a user that is not recognized by the system attempts to use the phone, perceived differences in the moisture signature (possibly in combination with thermal and velocity signatures and with recognition of speech using frequency and/or amplitude analysis) can prevent the phone from being unlocked. This is an additional safety feature.

Furthermore, the combination of sensor response with processes of filtering of audio signals may enable noise to be reduced. For example, the response of the sensor may be used in conjunction with signal processing to filter out audio signals that are not related to the user's speech (e.g., audio signals which are not correlated with moisture signals).

In some embodiments, the response of the sensor may also be used in conjunction with signal processing to process signals for the recognition of the user's mood. In one such exemplary embodiment, the processed signals may be correlated with a velocity signature of the user's breath. For example, some processed signals may be correlated to slow, deep breaths to indicate that the user was relaxed, while other processed signals may be correlated to rapid, irregular breaths to indicate that the user was stressed. A combination of the sensor and a microphone in a single device may further allow for measurements that provide complementary information, thereby providing improved results as compared to the use of a sensor alone. For example, the combination of a sensor with a microphone may allow for the processing of audio signals in such a manner so as to recognize a user's mood with greater detail and accuracy as compared to embodiments in which the sensor is used alone.

Accordingly, a touchless UI in the form of a speech recognition system includes a humidity sensor having an ultrafast response time, a low power consumption, and a high sensitivity to the moisture released by the user during speech.

Figure 1:
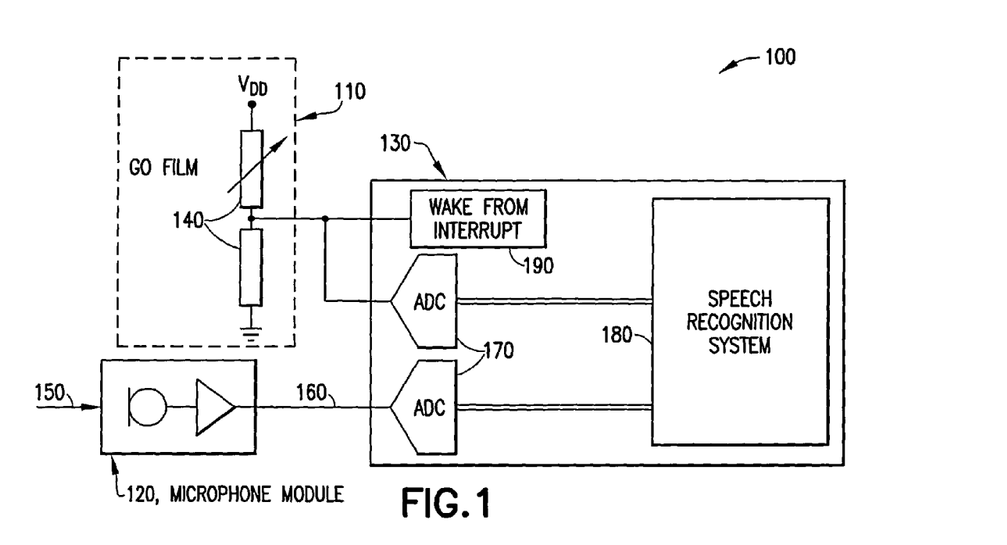
FIG. 1 is a schematic circuit diagram of one exemplary embodiment of a hybrid input device for a touchless user interface (UI), the device being in the form of a speech recognition system.

Referring now to FIG. 1, one embodiment of a circuit defining a UI in the form of a speech recognition system is designated generally by the reference number 100 and is hereinafter referred to as "system 100." System 100 may include a sensor 110, a microphone module 120, and a controller 130. The sensor 110 comprises a film 140 to which a rail voltage ($V_{DD}$) (e.g., from a power supply) is applied. The film 140 is capable of sensing humidity by detecting variations in electrical impedance which correspond to moisture gradients. The film 140 may comprise GO or any other material capable of sensing humidity by detecting variations in electrical impedance. In one exemplary embodiment, the film 140 includes a variable resistor and a fixed resistor, the fixed resistor generally providing a reference resistance value of about 10 mega ohms and not being limited as part of the layers defining the GO but possibly comprising a surface-mount metal film.

The microphone module 120, if present, incorporates a transducer that converts an auditory signal 150 to an electronic signal 160. In some embodiments, a protective screen may be located around the transducer of the microphone module 120, and the film 140 may be incorporated into this protective screen.

The controller 130 may include a processor 180, at least one type of memory, and software. The controller 130 may also include analog-to-digital converters (ADC) 170 that receive one or more electronic signals 160 from the transducer of the microphone module 120 and the film 140 and provide such signals as data input to the processor 180 for digital signal processing (DSP) by speech recognition algorithms. The controller 130 may also include an interrupt port 190 at which humidity sensed on the film 140 can be used to "awaken" the controller 130 from a "sleep" mode. The processor 180 may further include one or more switches as well as a means of receiving power.

The processor 180, in addition to providing DSP by the speech recognition algorithms, is capable of "sleeping" in a low-power mode that consumes only nanowatts of power. The processor 180 can be configured to be awakened when a direct current (DC) voltage across the interrupt port 190 increases above a preselected threshold value. This increase in DC voltage initiates the wake function and excites the sensor 110.

Figure 2:
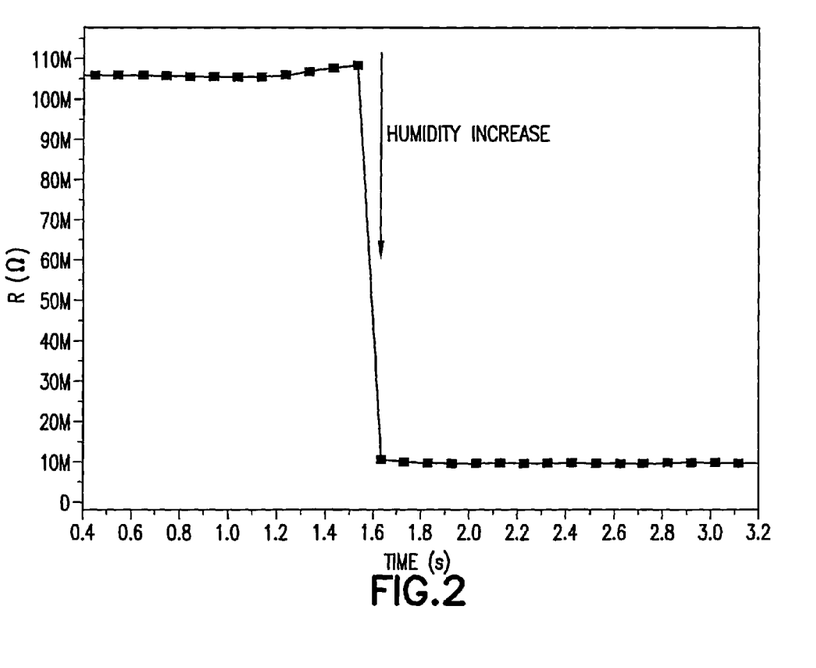
FIG. 2 is a graphical representation of a plot illustrating a response time of a thin graphene oxide (GO) film of the device of FIG. 1 to a humidity increase.

The excitation of the sensor 110 is achieved by decreasing a resistance of the film 140, which correspondingly increases the voltage. Referring now to FIG. 2, the resistance of the film 140 decreases when the user directs the auditory signal 150 to or at least breathes on the sensor 110 (and introduces humidity to the film 140), thereby allowing the voltage across the interrupt port 190 to correspondingly increase to activate the processor 180. This enables the operation of the system 100, including the sensor 110, the microphone module 120 (if included), and the speech recognition algorithms of the processor 180. Use of this humidity sensing aspect (instead of or in addition to sound) may provide a way to avoid false wake up triggers that may result from environmental noise or other environmental conditions, and it may also facilitate the reduction of noise during operation of speech recognition processes. Thus, the data input to the speech recognition algorithms is linked to the breath-controlled activation of the controller 180.

Figure 3:
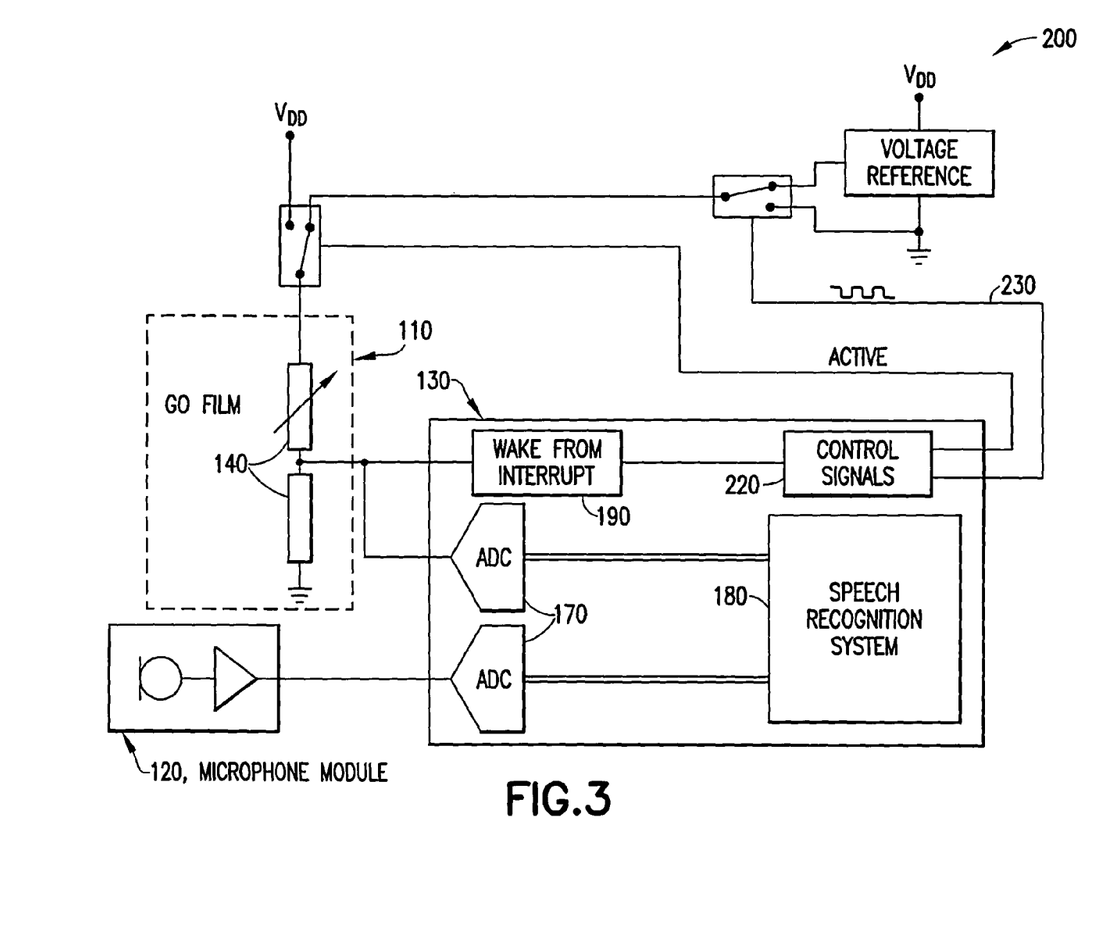
FIG. 3 is a schematic circuit diagram of another exemplary embodiment of a hybrid input device for a touchless UI, the device being in the form of a speech recognition system.

Referring now to FIG. 3, another embodiment of a UI in the form of a speech recognition system is designated generally by the reference number 200 and is hereinafter referred to as "system 200." In the circuit of system 200, excitation of the sensor 110 using DC voltage may be used for analysis of a breath signal of the user. In making such an analysis, a reading of the sensor value is obtained. However, unlike the circuit of system 100, excitation of the interrupt port 190 by DC voltage may not be suitable because offset voltages ($V_{off}$) may be introduced by either the sensor or the measurement electronics. These offset voltages ($V_{off}$) are typically small voltages introduced by either the sensor (e.g., due to charge trapping, electrochemical effects, changes in humidity and/or temperature), the measuring electronics (e.g., inaccuracies in the ADC, thermal changes affecting the value of the reference resistor), or the supply voltages (e.g., as other components attached to the same power supply switch on and off). Also, a rail voltage ($V_{DD}$) (e.g., from a power supply) may produce electronic noise, which may compromise operation of the system 200. Therefore, in the circuit of system 200, the DC excitation voltage from the interrupt port 190 is passed to a control mechanism 220 that transforms the DC excitation voltage to a square wave 230 when the system is awakened. The high voltage is set to a reference voltage ($V_{ref}$), and the low voltage is ground. A voltage difference measured by the ADC 170 is:

$$(V_{ref}+V_{off})R_{meas}/(R_{sense}+R_{meas})-V_{off}R_{meas}/(R_{sense}+R_{meas})=V_{ref}R_{meas}/(R_{sense}+R_{meas})$$

which is independent of offset voltage (where $R_{sense}$ is the resistance of the sensor 110 and $R_{meas}$ is the resistance of a series measurement resistor). The frequency of the square wave 230 is selected such that a parallel capacitance of the film 140 ($C_{sense}$) does not cause inaccuracies in the voltage measured by the ADC 170. More specifically, $1/R_{sense}C_{sense}$ or $1/R_{meas}C_{sense}$ is much larger than the measurement frequency to give the capacitor time to discharge before taking a reading.

Figure 4:
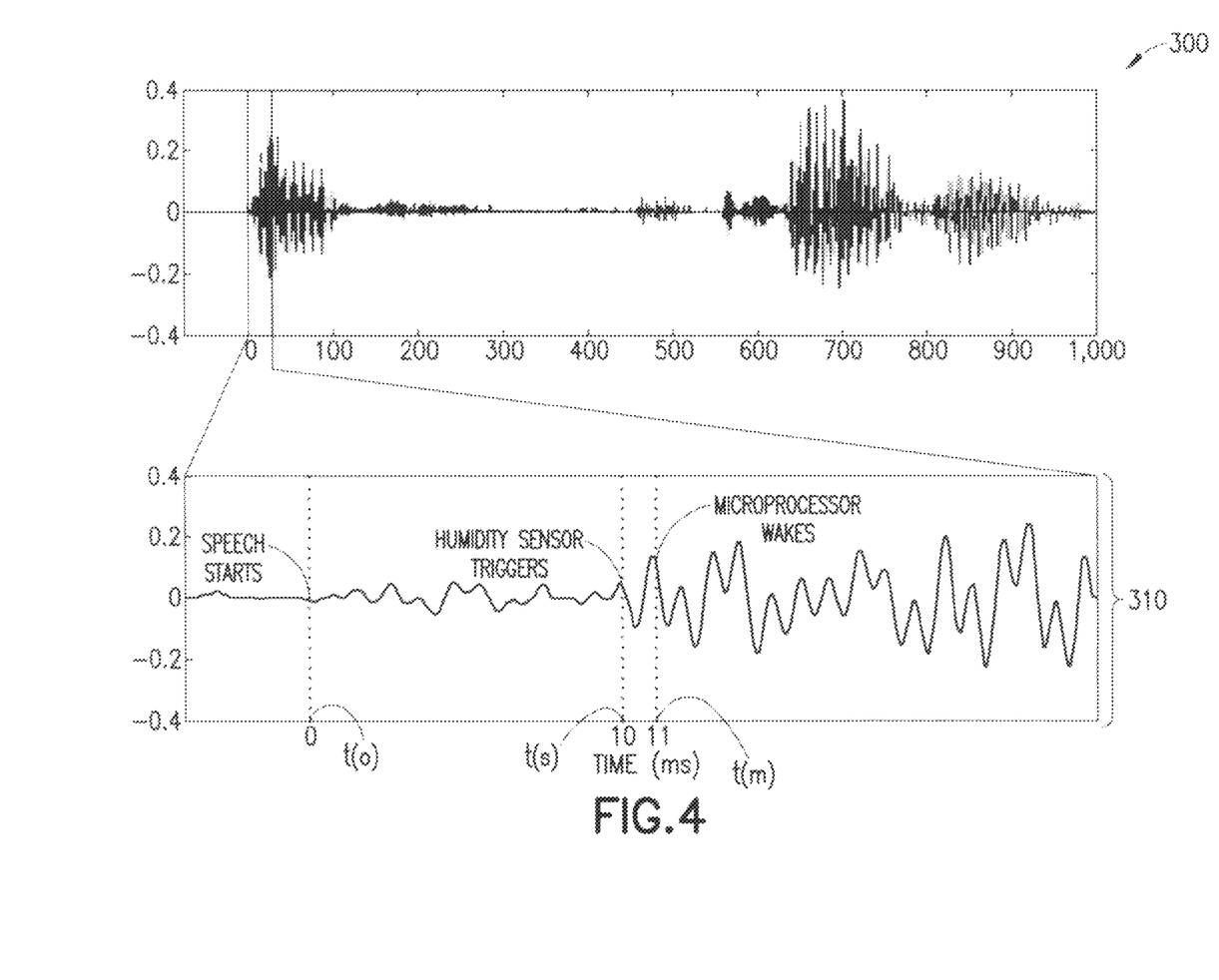
FIG. 4 is a graphical representation of a speech waveform of a voice command directed to a touchless UI in the form of a speech recognition system.

Referring now to FIG. 4, a speech waveform for a voice command having a one-second duration of time is shown generally at 300. An expanded portion of the speech waveform 300 is shown at 310. As shown in the expanded portion 310, the user's speech is started at time zero (to), and the response of the sensor 110 can be detected at $t_S$ (as low as about 10 ms). The time taken for the processor 180 to wake from sleep corresponds to $t_M$, which is the time taken for the processor's oscillator to start up and stabilize, which is typically about 1,000 clock cycles, or 1 ms for a 1 MHz clock speed. This means that the processor can be recording the speech and running speech recognition algorithms about 11 ms after the user starts to speak, which is suitably fast for speech-controlled user interfaces and suitably fast enough to record the majority of the speech waveform 300.

Once the processor 180 is awake, the ADCs 170 in communication with the sensor 110 and the microphone module 120 sample the respectively output signals. The speech recognition algorithms can then interpret (e.g., through DSP) the signals from the ADCs 170. Additional information from the sensor 110 can be correlated to the electronic signal 160 from the microphone module 120 to discriminate background noise from the auditory signal 150 when the user is talking.

In any embodiment, the sensor 110 can be made, for example, by spraying or inkjet printing a thin film 140 of GO on top of printed electrodes on a substrate (as a screen or in arrays), which could be easily integrated on a surface of the device. When integrated into the sensor 110, the film 140 is generally transparent.

Figure 5:
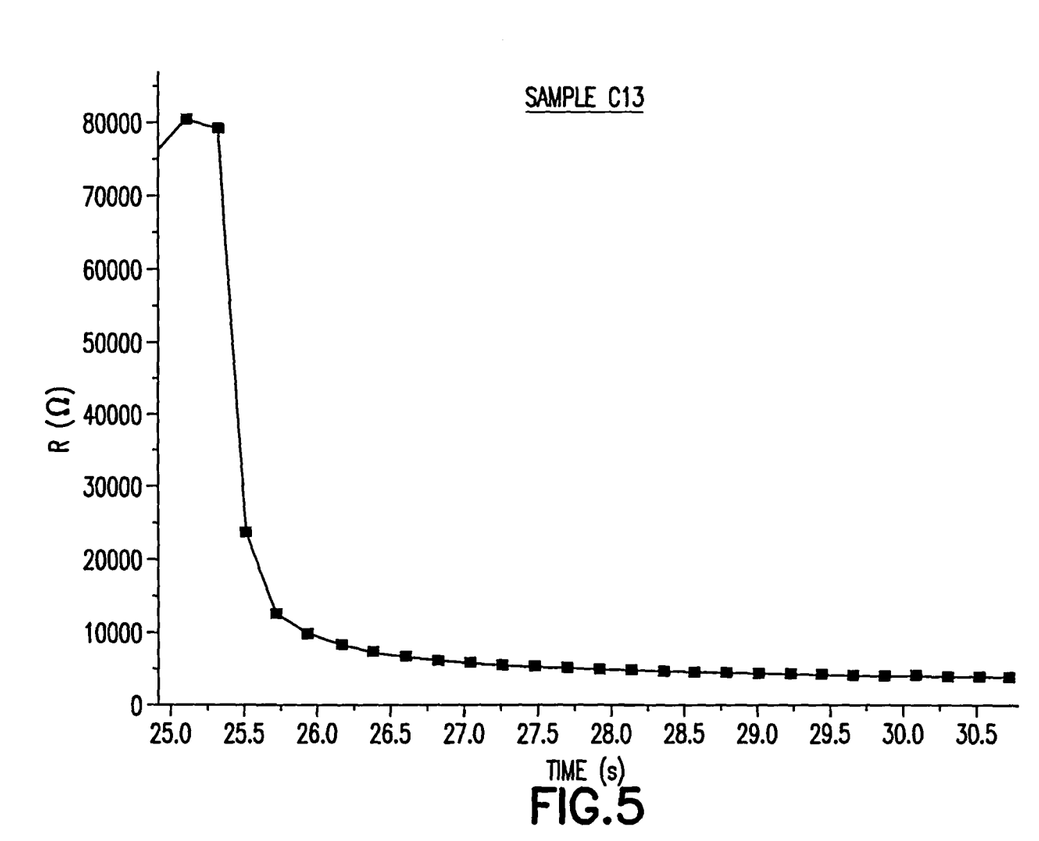
FIG. 5 is a graphical representation of a plot illustrating a response time of a drop cast GO film to a humidity increase.
Figure 6:
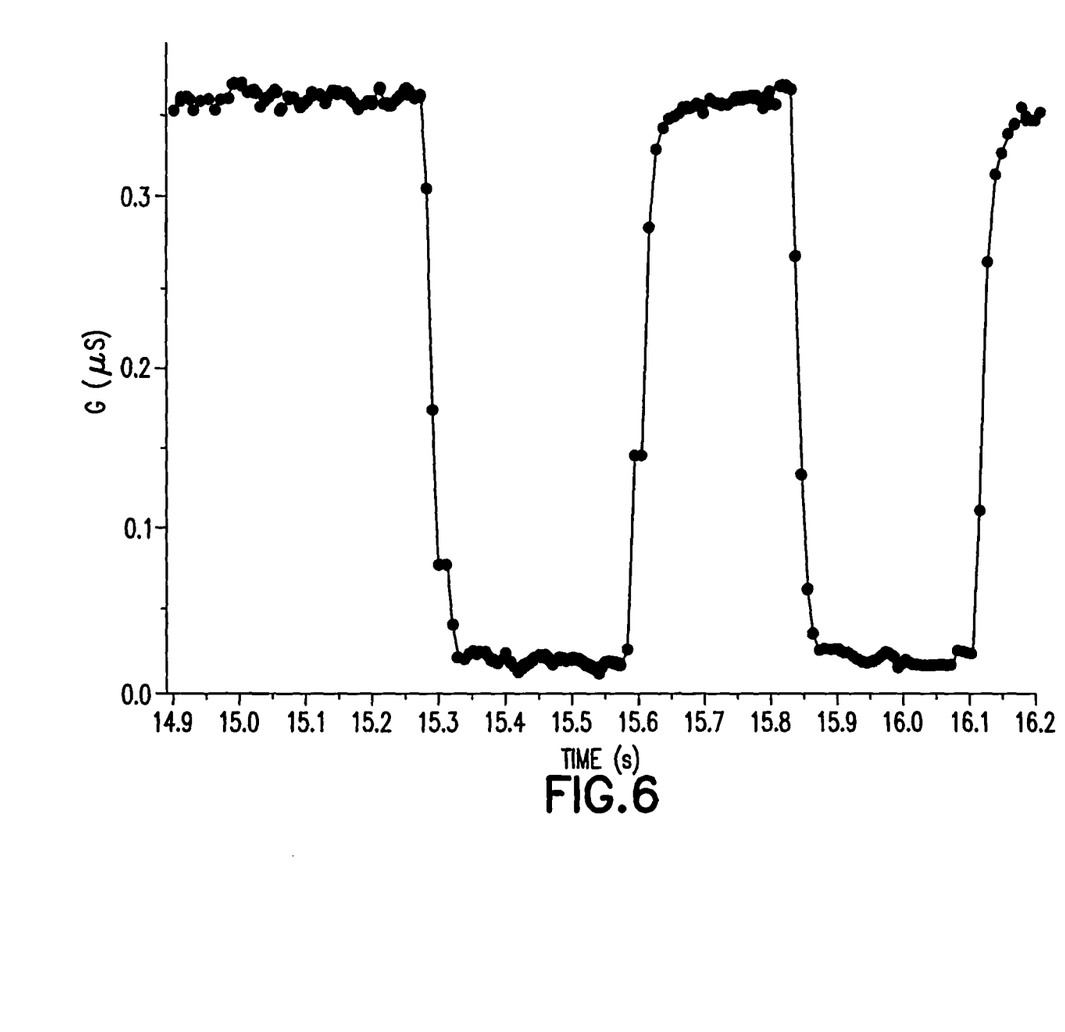
FIG. 6 is a graphical representation of a plot illustrating a response time of a sprayed GO film to humidity pulses.

The response time of a sensor 110 incorporating a film 140 of GO is found to be dependent on the GO film thickness: the response time decreases with decreasing the film thickness. For example, referring to FIG. 5, the response time of a drop cast GO film in which thickness is about 1 micrometer (um) can be about 600 ms, whereas, referring to FIG. 6, the response time of a sprayed GO film in which the thickness is about 15 nanometers (nm) can be about 40 ms. Due to the two-dimensional nature of the GO flakes, a GO film having a thickness equal to one atomic plane (which can be about 1 nm) can be achieved, for example, using a Langmuir-Blodgett technique. Therefore, a response time much smaller than 40 ms (for example as low as 10 ms or less) can be achieved with ultrathin GO films.

Figure 7:
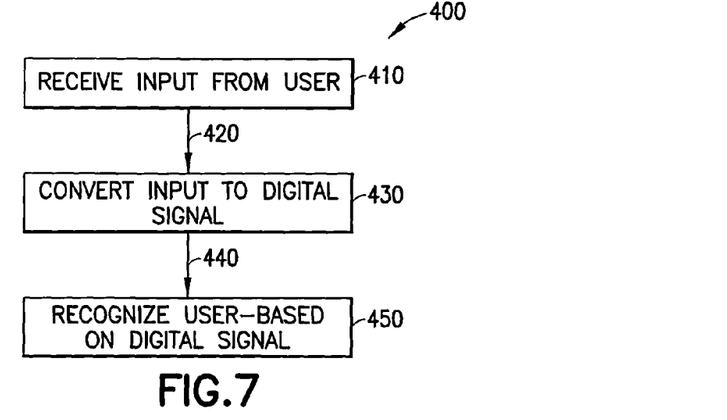
FIG. 7 is a diagram illustrating an exemplary method of using a touchless UI in the form of a speech recognition system.

Referring now to FIG. 7, one exemplary method of using a UI in the form of a speech recognition system that includes a hybrid user input device is designated generally by the reference number 400 and is hereinafter referred to as "method 400." Method 400, which may be defined by software and embodied on a non-transitory storage medium of a computer, comprises a receiving step 410 in which an input is received from the user. In the receiving step 410, the input may be non-tactile (touchless) and in the form of at least a breath from the user. The breath may or may not have an auditory component. From the receiving step 410, a signal 420 is passed to a conversion step 430.

In the conversion step 430, humidity from the breath input of the user is introduced to the film 140 to produce a signal that allows for the activation of the processor 180. Simultaneously or nearly simultaneously, the breath input is converted to a digital signal by the ADC 170. Optionally, the signal that allows for the activation of the processor 180 may be fed back to the receiving step 410 as a square wave 230 to compensate for noise produced by the offset voltages and the rail voltage.

The digital signal, shown at 440, is then passed to the speech recognition algorithms of the processor 180 to be processed in a processing step 450. In the processing step 450, changes in profiles of various signals input from the user may be analyzed, for example, to determine user identification, mood recognition of the user, and the like.

Figure 8:
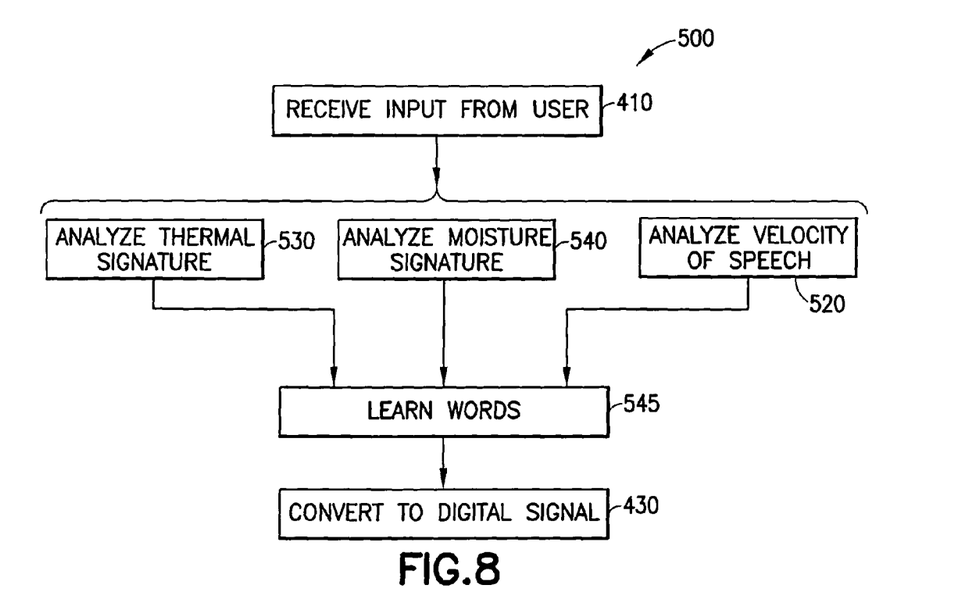
FIG. 8 is a diagram illustrating an exemplary method of processing signals of the method of FIG. 7.

Referring now to FIG. 8, one exemplary method of processing the signals of the UI is designated generally by the reference number 500 and is hereinafter referred to as "method 500." In method 500, the input from the receiving step 410 is analyzed in one or more of a velocity of speech analysis step 520, a thermal signature analysis step 530, and a moisture signature analysis step 540. Output analysis from one or more of the velocity of speech analysis step 520, the thermal signature analysis step 530, and the moisture signature analysis step 540 is used in a learning step 545 in which the sensor 110 learns words to distinguish different emotions of the user.

In one example, an apparatus comprises a sensor comprising a sensing film configured to provide a signal based upon a user's breath and a controller operably associated with the sensor. The controller is configured to receive the signal based upon the user's breath.

In another example, an apparatus comprises a breath sensor comprising a graphene oxide film configured to sense a variation in electrical impedance based upon a moisture gradient and output the sensed variation as an output signal and a controller configured to process the output signal from the breath sensor. The apparatus is configured to receive the output signal from the breath sensor and provide a signal in response thereto.

In another example, a method comprises providing a user interface comprising a sensor that includes a film configured to provide a signal as a result of moisture, and a controller operably associated with the sensor, the controller comprising a processor; receiving an input from a user at the user interface, the input comprising moisture in the form of humidity from a breath from the user; producing the signal from the input based upon the breath of the user; and receiving the signal produced from the input from the breath of the user at the processor and processing the signal.

In another example, a non-transitory computer readable storage medium comprises one or more sequences of one or more instructions which, when executed by one or more processors of an apparatus, cause the apparatus to at least receive an input from a user, the input comprising moisture in the form of humidity based upon a breath from the user; produce a signal from the input based upon the breath of the user; and receive the signal produced from the input based upon the breath of the user at a processor and process the signal.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications, and variances which fall within the scope of the appended claims.

What is claimed is:

1. An apparatus, comprising:
   a sensor comprising a sensing film configured to provide a signal based upon a user's breath; and
   a controller operably associated with the sensor, where the controller is configured to receive the signal based upon the user's breath;
   where the signal based upon the user's breath is a variation in electrical impedance received on the sensing film; and
   where the variation in electrical impedance is a decrease over a short period of time.

2. The apparatus of claim 1, further comprising a microphone operably associated with the controller.

3. The apparatus of claim 1, where the sensing film is selected from the group consisting of graphene oxide, graphene, functionalized graphene, fluorographene, molybdenite, boron nitride, and combinations of the foregoing.

4. The apparatus of claim 1, where the controller includes a speech recognition system.

5. The apparatus of claim 1, where the controller includes a means for analyzing a velocity of a selected portion of speech of the user.

6. The apparatus of claim 1, where the controller includes a means for analyzing a thermal signature of a selected portion of the user's breath.

7. The apparatus of claim 1, where moisture released from the user's breath is used for identification of the user.

8. The apparatus of claim 1, where the controller comprises a means for signal processing that filters out at least a portion of the signal from the sensor.

9. The apparatus of claim 1, where the sensor senses humidity in the user's breath.

10. The apparatus of claim 1, where the received signal based upon the user's breath awakens a component of the apparatus from a sleep mode.

11. The apparatus of claim 1, where the short period of time over which the decrease occurs is about 10 to 12 milliseconds.

12. An apparatus, comprising:
    a breath sensor comprising a film configured to sense a variation in electrical impedance based on a moisture gradient and output the sensed variation as an output signal; and
    a controller configured to process the output signal from the breath sensor;
    where the apparatus is configured to receive the output signal from the breath sensor and provide a signal in response thereto; and
    where the variation in electrical impedance is a decrease over a short period of time.

13. The apparatus of claim 12, where the controller includes a speech recognition system.

14. The apparatus of claim 12, where the signal provided in response to the user's breath awakens the controller from a sleep mode.

15. The apparatus of claim 12, further comprising a control mechanism associated with the controller, the control mechanism being configured to transform the signal from the breath sensor to a square wave.

16. The apparatus of claim 12, further comprising a microphone operably associated with the controller, the microphone being configured to receive an auditory signal from the user, the auditory signal being transformed into an electronic signal that can be used for at least one of user identification and mood recognition of the user.

17. A method, comprising:
    providing a user interface comprising a sensor that includes a film configured to provide a signal as a result of moisture, and a controller operably associated with the sensor, the controller comprising a processor;
    receiving an input from a user at the user interface, the input comprising moisture in the form of humidity from a breath from the user;
    producing the signal from the input based upon the breath of the user; and
    receiving the signal produced from the input from the breath of the user at the processor and processing the signal;
    where the signal produced from the input based upon the breath of the user is a variation in electrical impedance received on the film; and
    where the variation in electrical impedance is a decrease over a short period of time.

18. The method of claim 17, where processing the signal at the processor comprises analyzing the signal from the input based upon the breath of the user to determine at least one of velocity of speech, thermal signature, and moisture signature.

19. The method of claim 18, where the determination of at least one of velocity of speech, thermal signature, and moisture signature is used to awaken the controller from a sleep mode.

20. A non-transitory computer readable storage medium, comprising one or more sequences of one or more instructions which, when executed by one or more processors of an apparatus, cause the apparatus to at least:
    receive an input from a user, the input comprising moisture in the form of humidity based upon a breath from the user;
    produce a signal from the input based upon the breath of the user; and receive the signal produced from the input based upon the breath of the user at a processor and process the signal;

wherein the signal from the input based upon the breath of the user is a variation in electrical impedance; and where the variation in electrical impedance is a decrease over a short period of time.

\* \* \* \* \*